United States Patent [19]
Kanamori

[11] Patent Number: 4,787,370
[45] Date of Patent: Nov. 29, 1988

[54] ATTACHMENT FOR ENDOSCOPES

[75] Inventor: Iwao Kanamori, Tokyo, Japan

[73] Assignee: Olympus Optical Co., Ltd., Tokyo, Japan

[21] Appl. No.: 49,322

[22] Filed: May 13, 1987

[30] Foreign Application Priority Data

May 14, 1986 [JP] Japan .............................. 61-72224[U]

[51] Int. Cl.$^4$ .............................................. A61B 1/06
[52] U.S. Cl. ........................................................ 128/6
[58] Field of Search ........................................ 128/4, 6

[56] References Cited

U.S. PATENT DOCUMENTS

| | | | |
|---|---|---|---|
| 1,751,584 | 3/1930 | Hansell | 128/4 X |
| 2,746,450 | 5/1956 | Lady et al. | 128/6 |
| 3,496,931 | 2/1970 | Pilling | 128/6 |
| 4,361,139 | 11/1982 | Takagi | 128/6 |
| 4,403,273 | 9/1983 | Nishioka | 128/6 X |
| 4,660,982 | 4/1987 | Okada | 128/6 X |

FOREIGN PATENT DOCUMENTS 57-89711  6/1982 Japan .

Primary Examiner—William H. Grieb
Attorney, Agent, or Firm—Cushman, Darby & Cushman

[57] ABSTRACT

In order to enable an endoscope to be made at a low cost and to provide the endoscope capable of effecting uniform illumination up to the peripheral regions of even a wide visual field without loss of the amount of light, the attachment for endoscopes is removably mountable to the forward end of the endoscope and comprised of an observation optical system and a light-guide member having a light-incidence end surface facing the illumination optical system of the endoscope for receiving a light coming therefrom and a light-emitting end surface having a shape different from that of the light-incidence end surface for emitting the above-mentioned light toward an object under observation.

11 Claims, 6 Drawing Sheets

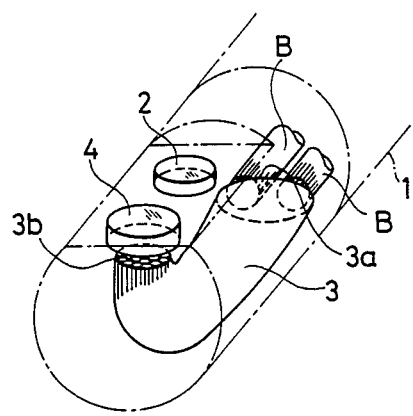
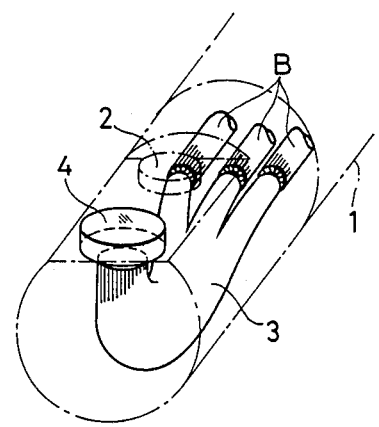
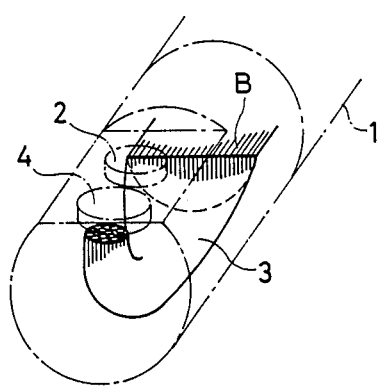

4,787,370

ATTACHMENT FOR ENDOSCOPES

BACKGROUND OF THE INVENTION (a) Field of the invention:

The present invention relates to an attachment which houses an observation optical system and an illumination optical system, and which is removably mounted at the foremost end portion of an endoscope such as fiberscope, non-flexible endoscope or electronic scope.

(b) Description of the prior art:

Endoscopes, in general, are such that various diversified component parts such as fiber bundles for observation, fiber bundles for illumination, a forceps channel, an air-supply tube, a water-supply tube, etc. require to be incorporated in a narrow tube of a diameter of the order of 10 mm at the largest. Therefore, it is the present state of art that all the necessary component parts may not be accomodated in a narrow tube unless the fill-up degree of these component parts is elevated by, for example, forming the cross sectional shape of the illumination fiber bundles not necessarily in a circular shape but, instead, making them in various other different shapes such as oval or semi-circular cross sections, and by winding them around a tube which supports the observation optical system, or by dividing the illumination fiber bundle into a plurality of narrow fiber bundles having such different cross sectional shapes as mentioned above and passing them through narrow spaces existing between a number of component parts.

In case the abovesaid attachment is disposed at the foremost end portion of an endoscope as stated above and in case the focal distance or the direction of visual field is intended to be altered, it will be noted that, in the event that the illumination fiber bundle B has a circular end surface and is bifurcated at the forward end portion of the endoscope body F as shown in FIGS. 1 and 2, not only the optical system 2 for switching over to the side-viewing which is aligned with the observation optical system O provided within the endoscope body F, but also the illumination system which comprises two light-guide members 3, 3 both having a circular cross section and aligned with the illumination fiber bundles B, B, respectively, which jointly constitute the illumination optical system and which also comprises two illumination lenses 4, 4 provided, respectively, at the light-emitting ends of the respective light-guide members, has been constructed in the past in such a form as if the illumination optical system per se on the endoscope body F side is extended in its length, also within the attachment 1 which is removably mounted onto the endoscope body F.

As stated above, in the attachment of the conventional type mentioned above, there have been the problems bringing forth such an inconvenience as represented by an increase in the number of optical parts which, in turn, leads to an increase in the manufacturing cost, and not only that, but also the inconvenience that, when it is intended to provide an arrangement for a wide angle viewing, the outer diameter of the illumination lens becomes larger, and in case of, for example, side-viewing, the space per se of the region in which a lens is disposed is too narrow for the accomodation of an illumination lens and/or the observation lens, so that if, for example, the illumination lens is forcibly reduced in size for being accomodated in the predetermined space, this will lead to vignetting, by the illumination lens, of a part of the illumination light which is transmitted by the illumination fiber bundle, leading to an insufficient amount of light available in the peripheral regions of the visual field.

SUMMARY OF THE INVENTION

It is, therefore, a primary object of the present invention to provide an attachment for endoscopes, which is capable of solving those problems mentioned above.

According to the present invention, the attachment is such that the light-incidence end surface thereof is provided in such a number and shape as to correspond to the number and the end surface shape of the illumination fiber bundles located on the endoscope body side, and the the light-emitting end surface is composed of a light-guide member formed to provide a single surface which is different in shape from the light-incidence end surface, whereby making it possible to appropriately select the shape of the light-emitting end surface in compliance with the direction of illumination and the extend of illumination and also with the size of the space for installing the light-guide member, independently of the number and the shape of the light-incidence end surface.

Another object of the present invention is to provide an endoscope which can be manufactured at a low cost.

A further object of the present invention is to provide an illumination optical system for endoscopes, which is capable of realizing uniform illumination as far as the peripheries of the visual field without a loss of the amount of light even where the extent of the visual field is large.

These and other objects as well as the features and the advantages of the present invention will be apparent from the following detailed description of the preferred embodiments when taken in conjunction with the accompanying drawings.

BRIEF DESCRIPTION OF THE DRAWINGS

FIGS. 8 to 14 are perspective views of the essential portions of mutually different further embodiments of the present invention.

DETAILED DESCRIPTION OF THE PREFERRED EMBODIMENTS

Figure 1:
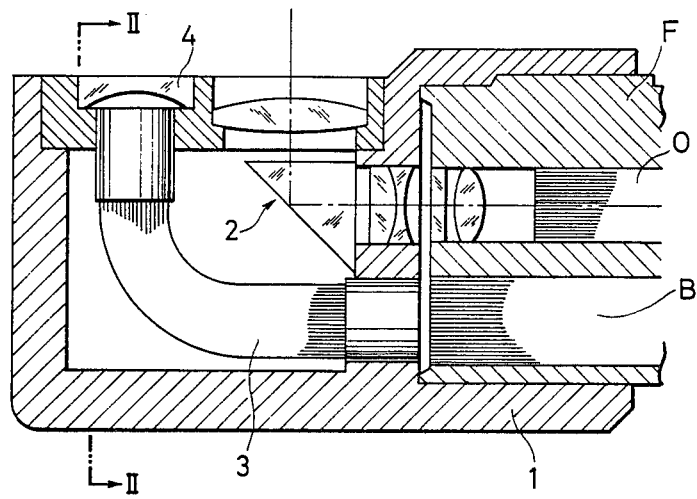
FIG. 1 is a sectional view showing a conventional example of the attachment mounted to the foremost end portion of an endoscope.
Figure 2:
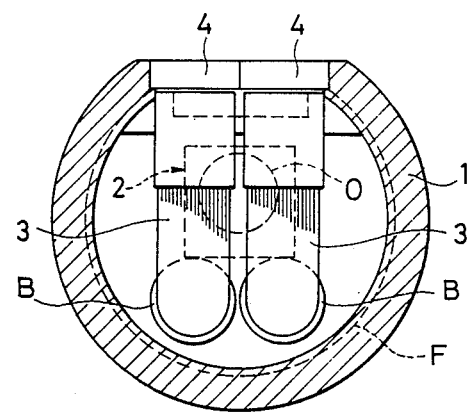
FIG. 2 is a sectional view taken along the line II—II of FIG. 1.

Description will hereunder be made, in a concrete fashion, of the present invention based on the illustrated respective embodiments, by assigning same reference numerals and symbols to parts which are identical or similar to those of the conventional example.

Figure 3:
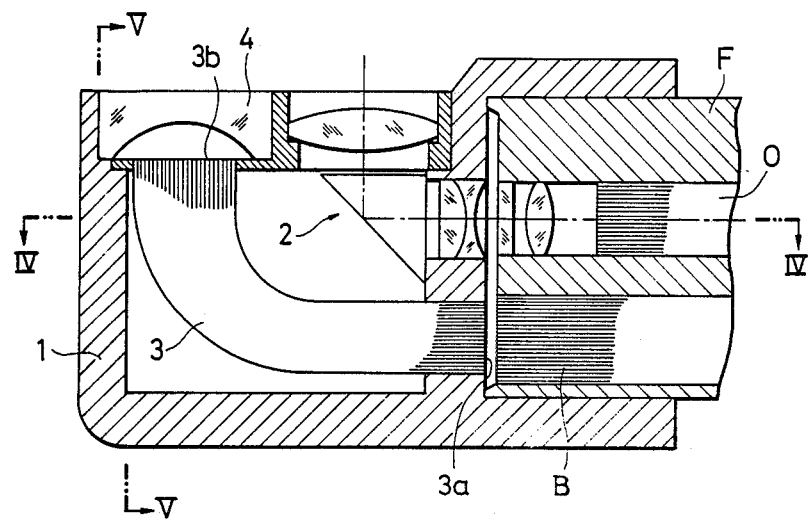
FIG. 3 is a sectional view showing an embodiment of the attachment according to the present invention which is mounted to the forward end portion of an endoscope.
Figure 4:
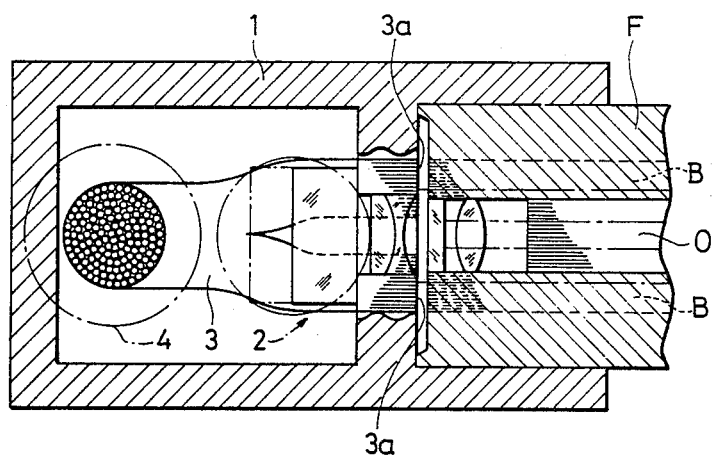
FIG. 4 is a sectional view taken along the line IV—IV of FIG. 3.
Figure 5:
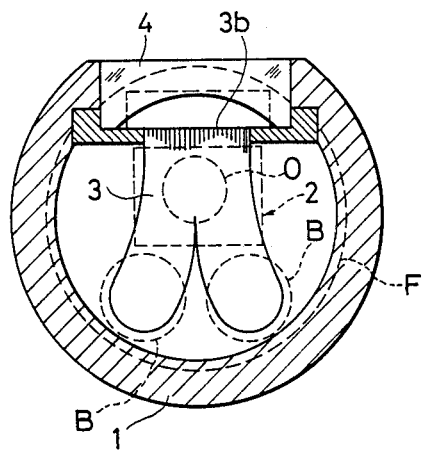
FIG. 5 is a sectional view taken along the line V—V of FIG. 3.

FIGS. 3 to 5 show a first embodiment of the present invention. This embodiment is shown in the state that an attachment 1 is mounted to the forward end of a fiberscope body F of a cylindrical shape. In this state, the side-view switching observation optical system 2 provided within the attachment 1 is aligned with an observation optical system O containing an objective lens located within the fiberscope body F. Also, a light-incidence end surface 3a of a light-guide member 3 which is comprised of a fiber bundle within the attachment 1 is bifurcated, and the divided fiber bundles are aligned with the illumination optical systems, respectively, which are comprised of two fiber bundles B, B both having a circular cross section and being provided within the fiber scope body F. The light-emitting end surface 3b of the light-guide member 3 is integrated as a single circular end surface, and an illumination lens 4 having a diameter greater than that of the light-emitting end surface 3b is disposed at said light-emitting end.

Figure 6:
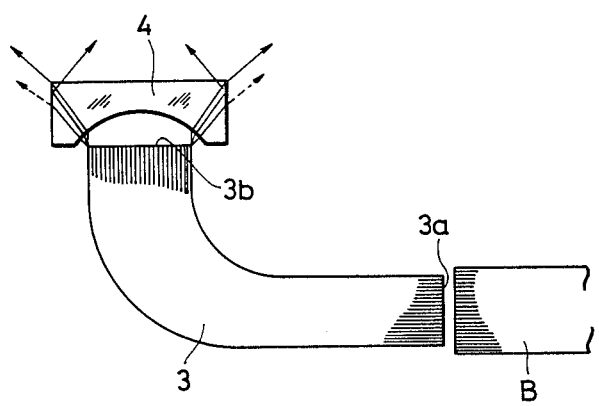
FIG. 6 is an explanatory illustration showing the state in which the illumination light is emitted from the illumination lens.

The first embodiment of the present invention is constructed as described above. Therefore, the illumination light beams emitting from the two fiber bundles B, B provided within the fiberscope body F impinge onto the two light-incidence end surfaces 3a, 3a, respectively, of the light-guide member 3 provided within the attachment 1, and the direction of advancement of these light beams is altered upwardly for 90° and these light beams are caused to emit through a single light-emitting end surface 3b, and the resulting emitting light reaches a predetermined range of the surface of the object under observation by the illumination lens 4. As such, according to this instant embodiment, the provision of the illumination lens 4 in a single number is enough always. Thus, not only is it possible to reduce the manufacturing cost, but also the diameter of the illumination lens 4 can be made greater for the diameter of the light-emitting end surface 3b. As a result, it is possible to reduce those light rays which transmit through the outer circumferential surface of the illumination lens 4 without undergoing total reflection, as shown in FIG. 6, thereby to prevent the loss of amount of light in the peripheral areas of the extend of illumination.

Figure 7:
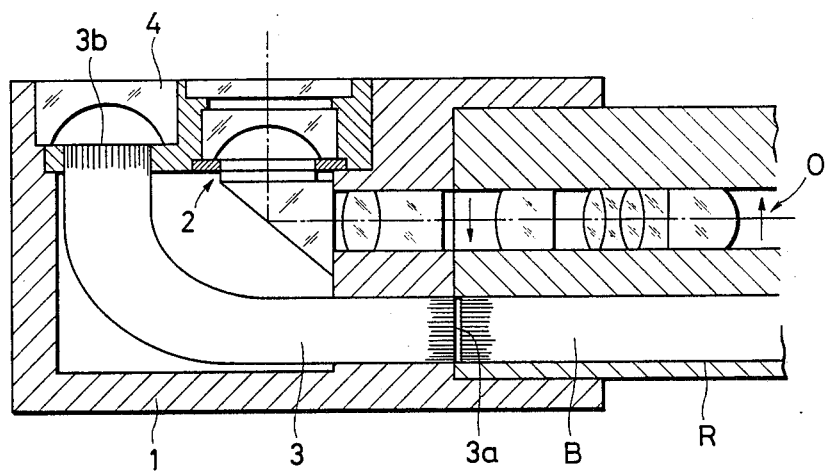
FIG. 7 is a sectional view showing another embodiment of the present invention.

FIG. 7 shows a second embodiment of the present invention. This embodiment is such that the attachment 1 is constructed so as to be suitable for non-flexible endoscopes. That is, in the state that the attachment 1 is mounted to a non-flexible endoscope body R of a cylindrical shape, the side-view observation optical system 2 on the attachment side 1 is aligned with the observation optical system O on the non-flexible endoscope side. And, the bifurcated light-incidence end surfaces 3a, 3a (which, in the drawing are illustrated by one of them) of the light-guide member 3 on the attachment 1 side are aligned with the illumination optical systems, respectively, which are comprised of two fibers bundles B, B (in the drawings, only one of them is shown) on the non-flexible endoscope side. Furthermore, an illumination lens 4 having a diameter greater than that of the single light-emitting end surface 3b is disposed at the light-emitting end of the light-guide member 3 which is integrated into a single member. In this instant second embodiment also, its function and effect are identical with those of the first embodiment, and therefore the description thereof is omitted.

Figure 8:
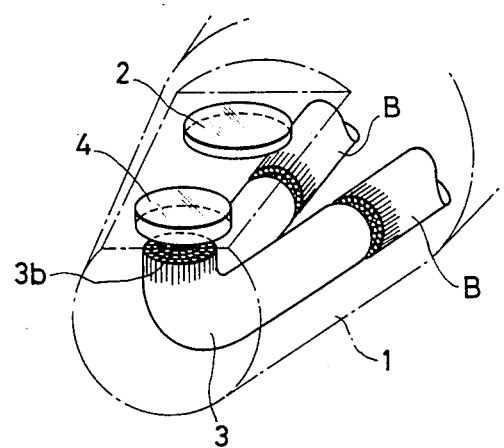

FIG. 8 shows a third embodiment of the present invention. This embodiment differs from the first embodiment in that the forward end portion of the attachment 1 is formed in a frusto-conical shape and that the illumination lens 4 is so selected as to have a diameter identical with or somewhat larger than that of the light-emitting end surface 3b of the light-guide member 3 in compliance with the narrowing of the installment space. The remainder of arrangement as well as the function and effect of this instant embodiment are same as those of the first embodiment. Therefore, their description is omitted.

FIG. 9 shows a fourth embodiment of the present invention. This embodiment differs from the first embodiment in that the light-incidence end surface 3a of the light-guide member 3 is formed in a single oval shape having a largeness corresponding to the circular light-emitting end surfaces of the two fiber bundles B, B on the fiberscope side. In this instance, however, the arrangement can further contribute to the reduction of the manufacturing cost.

FIG. 10 shows a fifth embodiment of the present invention. This instant embodiment differs from the first embodiment in that, while the illumination optical system on the fiberscope side is constructed with three fiber bundles B each having a circular cross section, the light-guide member 3 in the attachment 1 has trifurcated light-incidence end surfaces to comply with the end surfaces of the three fiber bundles B.

FIG. 11 shows a sixth embodiment of the present invention. This embodiment differs from the fourth embodiment of FIG. 7 in that, while the illumination optical system on the fiberscope side is constructed with a fiber bundle B having a semi-circular cross section, the light-guide member 3 in the attachment 1 has its light-incidence end surface formed in a semi-circular shape so as to comply with the cross-sectional shape of the illumination optical system.

Figure 12:
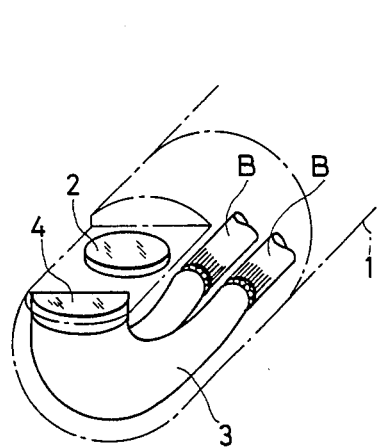

FIG. 12 shows a seventh embodiment of the present invention. This instant embodiment differs from the first embodiment in that the forward end portion of the attachment 1 is formed in a tapered fashion as illustrated. In compliance therewith, the light-emitting end surface of the light-guide member 3 and the illumination lens 4 are shaped in a correspondingly tapered shape, i.e. in such a shape as if an oval is cut into half along the short diameter thereof. Thus, in this instant embodiment, an illumination lens 4 can be disposed effectively in a space of a limited shape.

Figure 13:
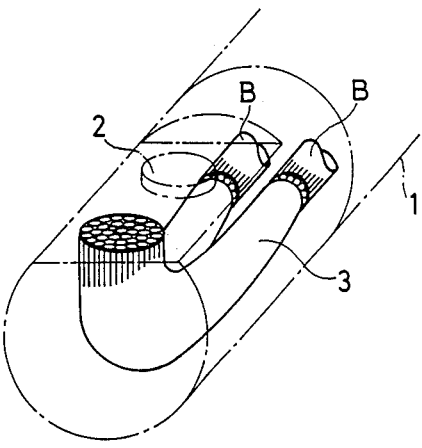

FIG. 13 shows an eighth embodiment of the present invention. This embodiment differs from the first embodiment in that the illumination lens is omitted so that the limited space can be effectively utilized.

Figure 14:
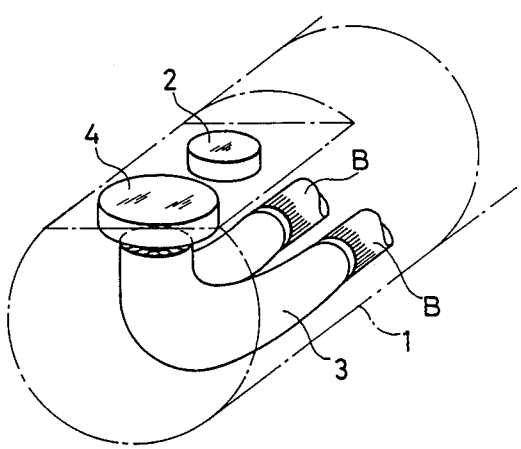

FIG. 14 shows a ninth embodiment of the present invention. This instant embodiment differs from the first embodiment in that the light-guide member 3 is comprised of a single fiber.

In the above-mentioned respective embodiments, description has been made with respect to the instances which are arranged invariably in such a fashion that the direction of the visual field of the observation optical system in either the fiberscope or the non-flexible endoscope is altered upwardly for 90° by means of the attachment 1, and that along therewith the direction of the advancement of the illumination light is altered also upwardly for 90° to thereby be suited for the so-called side-viewing. It should be noted, however, that the present invention is not limited to these embodiments of the above-described arrangement. Also, the light-guide member may be constructed with such a material as plastics or glass, aside from the above-described embodiments. Also, it will be needless to say that the present invention can be applied to electronic endoscopes, etc.

According to the present invention, as stated above, it should be noted that, whatever the arrangement or the configuration of the light-guide which constitutes the illumination optical system in endoscopes, i.e. fiber-scope, non-flexible endoscope, electronic-scope, etc. may be, it is possible to fabricate the assembly in such a way that only a single piece of illumination lens is enough ultimately. Thus, it is possible to reduce the manufacturing cost. Moreover, there can be provided an illumination optical system which is capable of illumination uniformly up to the peripheral regions of the visual field without a loss of the amount of light even in case of a large extend of visual field within a limited space.

What is claimed is:

1. An attachment for endoscopes removably mountable to the forward end of an endoscope provided with, within the forward end thereof, an illumination optical system having a plurality of light-emitting ends arranged separately each other, in which said attachment comprises a light guide member having light-incidence end means capable of receiving lights coming from each of said plurality of light-emitting ends when the attachment is mounted to the forward end of the endoscope and having a single light-emitting end surface capable of emitting said lights having been received by said light-incidence end means toward an object under observation.

2. An attachment for endoscopes according to claim 1, in which:
    said attachment further comprises an observation optical system capable of being aligned with an observation optical system of said endoscope when said attachment is mounted to the forward end of said endoscope.

3. An attachment for endoscope according to claim 1, in which:
    said light-incidence end means is formed as a single light-incidence surface covering all of said light-emitting ends.

4. An attachment for endoscopes according to claim 1, in which:
    said light-incidence end means is formed as a plurality of light-incidence surfaces respectively receiving the lights coming from each of said light-emitting ends.

5. An attachment for endoscopes according to claim 3 or 4, in which:
    said light-guide member is constructed with optical fibers.

6. An attachment for endoscopes according to claim 3 or 4, in which:
    said light-incidence surface is of a circular shape.

7. An attachment for endoscopes according to claim 3 or 4, in which:
    said light-guide member is constructed with a single fiber.

8. An attachment for endoscopes according to claim 3 or 4, in which said light-incidence surface is of an oval shape.

9. An attachment for endoscopes according to claim 3 or 4, in which said light-incidence surface is of a semi-circular shape.

10. An attachment for endoscope according to claim 3 or 4, in which said light-incidence surface is of a shape that an oval is cut into half along its short diameter.

11. An attachment for endoscopes removably mountable on the forward end of an endoscope and having a light-guide member having a light-incidence end means facing a light-emitting end of an illumination optical system of the endoscope when the attachment is mounted on the forward end of the endoscope to thereby be able to receive light coming from the light-emitting end and also having a single light-emitting end surface capable of emitting said light toward an object under observation, wherein said light-incidence end means has a shape differing from that of the light-emitting end surface, said light-incidence end means being divided into a plurality of pieces each being of a circular shape.

* * * * *